(12) United States Patent
Shimmura et al.

(10) Patent No.: US 9,347,042 B2
(45) Date of Patent: May 24, 2016

(54) METHOD FOR PRODUCING CORNEAL ENDOTHELIAL CELL

(71) Applicant: KEIO UNIVERSITY, Tokyo (JP)

(72) Inventors: Shigeto Shimmura, Tokyo (JP); Shin Hatou, Tokyo (JP); Kazuo Tsubota, Tokyo (JP); Satoru Yoshida, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 14/349,961

(22) PCT Filed: Oct. 5, 2012

(86) PCT No.: PCT/JP2012/076048
§ 371 (c)(1),
(2) Date: Apr. 4, 2014

(87) PCT Pub. No.: WO2013/051722
PCT Pub. Date: Apr. 11, 2013

(65) Prior Publication Data
US 2014/0315305 A1 Oct. 23, 2014

(30) Foreign Application Priority Data

Oct. 6, 2011 (JP) ................................ 2011-222138
Mar. 29, 2012 (JP) ................................ 2012-076080

(51) Int. Cl.
C12N 5/079 (2010.01)
A61L 27/38 (2006.01)
C12N 5/071 (2010.01)
A61K 35/00 (2006.01)

(52) U.S. Cl.
CPC ............ *C12N 5/0621* (2013.01); *A61L 27/3808* (2013.01); *A61L 27/3895* (2013.01); *C12N 5/069* (2013.01); *A61K 35/00* (2013.01); *A61L 2430/16* (2013.01); *C12N 2501/11* (2013.01); *C12N 2501/115* (2013.01); *C12N 2501/15* (2013.01); *C12N 2501/235* (2013.01); *C12N 2501/33* (2013.01); *C12N 2501/385* (2013.01); *C12N 2501/727* (2013.01); *C12N 2501/999* (2013.01); *C12N 2506/08* (2013.01); *C12N 2506/09* (2013.01); *C12N 2506/45* (2013.01); *C12N 2533/54* (2013.01)

(58) Field of Classification Search
CPC .......................... A61K 35/30; C12N 2506/094
See application file for complete search history.

(56) References Cited

U.S. PATENT DOCUMENTS 7,959,939 B2 6/2011 Yamagami et al.
2005/0214259 A1 9/2005 Sano et al.
2007/0238173 A1 10/2007 Yamagami et al.
2012/0207744 A1* 8/2012 Mendlein et al. .......... 424/130.1
2013/0023050 A1 1/2013 Shima et al.
2014/0127803 A1* 5/2014 Hayashi et al. ............... 435/373
2014/0170751 A1* 6/2014 Hayashi et al. ............... 435/377

FOREIGN PATENT DOCUMENTS

EP 2532738 A1 12/2012
JP 2004-024852 A 1/2004
JP 2005-229869 A 9/2005
JP 2009-268433 A 11/2009
WO WO 2011/096593 A1 8/2011

OTHER PUBLICATIONS

Ittner L. et al. Compound Developmental Eye Disorders Following Inactivation of TGFbeta Signaling in Neural Crest Stem Cells. J of Biology 2005:4(11).*
Stepp M. Corneal Integrins and Their Functions. Experimental Eye Research 83:3-15, 2006.*
Takacs L. et al. Stem Cells of the Adult Cornea. Cytometry part A, 75A:54-66, 2009.*
Yoshida S. et al. Generation of Stratified Squamous Epithelial Cells from Induced Pluripotent Stem Cells. ARVO Annual Meeting Abstract vol. 2011, p. 5138, May 2011.*
Aggarwal et al., *Br. J. Ophthalmol.*, 81: 178-179 (1997).
Hato et al., *Japan Cornea Society Sokai—Keratoplasty Society of Japan Program Shorokushu*, 35(27): 59, Abstract No. 68 (Feb. 2011).
Hato et al., *Regenerative Medicine*, 10(supplemental): 163, Abstract No. O-17-1 (Feb. 1, 2011).
Lee et al., *Nature Protoc.*, 5(4): 688-701 (2010).
Price et al., *Journal of Refractive Surgery*, 21(4): 339-345 (2005).
Shimmura et al., *Cornea*, 24(2): 178-181 (2005).
Toma et al., *Nat. Cell. Biol.*, 3(9): 778-784 (Sep. 2001).
Yoshida et al., *Stem Cells*, 24(12): 2714-2722 (2006).
Japanese Patent Office, International Search Report in International Patent Application No. PCT/JP2012/076048 (Jan. 8, 2013).
Hatou et al., *Stem Cells and Development*, 22(5): 828-839 (2013).
Ju et al., *PLoS One*, 7(7): e42378 (2012).
Kumar et al., *Developmental Biology*, 340(1): 67-74 (2010).
Okumura et al., *Investigative Ophthalmology & Visual Science*, 50(8): 3680-3687 (2009).
European Patent Office, Supplementary European Search Report in European Patent Application No. 12837799 (Oct. 7, 2015).

* cited by examiner

*Primary Examiner* — Ralph Gitomer
(74) *Attorney, Agent, or Firm* — Leydig, Voit & Mayer, Ltd.

(57) ABSTRACT

The invention provides a method of efficiently producing corneal endothelial cells, particularly from corneal stroma or iPS cell-derived neural crest stem cells, a method of producing corneal endothelial cells stably in a large amount by inducing more efficient differentiation of stem cells into corneal endothelial cells, and a medicament containing corneal endothelial cells. The method of inducing differentiation of stem cells into corneal endothelial cells includes a step of culturing the stem cells in a differentiation induction medium containing a GSK3 inhibitor (preferably a GSK3β inhibitor) and retinoic acid, with the differentiation induction medium preferably further containing one or more of TGFb2, insulin, a ROCK inhibitor, and the like.

16 Claims, 8 Drawing Sheets

A  eye transplanted with corneal endothelial sheet induced from COPs

B  control eye (endothelium detachment)

C  changes in corneal thickness

D  changes in intraocular pressure eye transplanted with corneal endothelial sheet induced from iPS cells control eye (endothelium detachment)

human COPs | corneal endothelial sheet induced from COPs eye transplanted with corneal endothelial sheet induced from COPs control eye (endothelium detachment)

changes in corneal thickness changes in intraocular pressure mouse SKPs corneal endothelial sheet induced from SKPs eye transplanted with corneal endothelial sheet induced from SKPs control eye (endothelium detachment)

changes in corneal thickness low magnification (x4)  high magnification (x20)

METHOD FOR PRODUCING CORNEAL ENDOTHELIAL CELL

CROSS-REFERENCE TO RELATED APPLICATIONS

This patent application is the U.S. national phase of International Patent Application No. PCT/JP2012/076048, filed Oct. 5, 2012, which claims the benefit of Japanese Patent Application No. 2011-222138, filed on Oct. 6, 2011, and Japanese Patent Application No. 2012-076080, filed on Mar. 29, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,391 bytes ASCII (Text) file named "716545ReplacementSequenceListing.txt," created Jul. 1, 2014."

TECHNICAL FIELD

The present invention relates to a method of producing a corneal endothelial cell from a stem cell, and a method of inducing differentiation of a corneal endothelial cell from a stem cell. Furthermore, the present invention relates to a corneal endothelial cell obtained by the method, a medicament using the same and the like.

BACKGROUND ART

The visual information is recognized when the light that entered from the cornea, which is a transparent tissue on the frontmost surface of the eyeball, reaches the retina to excite the retinal nerve cell, and the developed electric signals reach the visual field in the cerebrum via optic nerve. In other words, the cornea is positioned in front of a path where the light passes when a living organism receives visual information. Therefore, the turbidity in the cornea caused by damage and the like has a serious influence on the visual function.

Histologically, the cornea has a three-layer structure of corneal epithelium, corneal stroma, and corneal endothelium from the outer surface side. The transparency of cornea is maintained since the water content is kept constant by $Na^+$ active transport (pump function) by Na, K-ATPase and barrier function (tight junction protein such as ZO-1 and the like) in the corneal endothelium.

The above-mentioned function of corneal endothelial cell is impaired by a damage to the corneal endothelium such as a decrease in the corneal endothelial cell and the like, thus resulting in the edema of the corneal stroma. This decreases transparency of the cornea, and reduces the eyesight. Such condition is called bullous keratopathy. In the meantime, it is known that human corneal endothelial cell once injured scarcely shows an ability to regenerate. When the corneal endothelial cells have decreased due to certain injury, an effective or, in some cases, sole treatment thereof is corneal transplantation. In fact, about half the number of applicable cases of corneal transplantation is for bullous keratopathy caused by corneal endothelial functional disorder.

At present, patients with corneal endothelium damage are treated by penetrating keratoplasty wherein the whole three-layer structure of corneal epithelium, corneal stroma and corneal endothelium is transplanted. While the penetrating keratoplasty is an established technique, the supply of cornea is short in Japan as the situation stands, and the rejection reaction poses a problem. To solve such problems, "part transplantation" involving transplantation of only the damaged tissue is becoming popular. Deep lamellar keratoplasty (DLKP) involving transplantation of only the epithelium and stroma of the donor while preserving corneal endothelium (non-patent documents 1 and 2), corneal endothelium transplantation involving transplantation of only the part cornea including endothelium (patent documents 1 and 2, non-patent document 3) and the like are known. However, in the case of corneal endothelium transplantation, for example, the source of supply of the material for, transplantation is still the corneal endothelium itself. Since the number of donor of cornea is limited, the problem of donor shortage cannot be overcome, like penetrating keratoplasty. Furthermore, since corneal endothelial cell is difficult to culture, preparation of cultured cells in a number sufficient for transplantation places a large burden in terms of time and cost.

In recent years, separation of cells, having characteristics of stem cell, from the mouse corneal stroma has been reported (non-patent document 4). This stem cell derived from the neural crest has an ability to also differentiate into a nerve cell, an adipocyte and the like by using a differentiation induction medium.

While it has been reported that adhesive culture of tissue stem cell/progenitor cell in a medium added with TGFb2 can induce differentiation of these cells into corneal endothelial cells (patent document 3), the presence or absence of the function as corneal endothelial cell (for example, pump function) is not shown.

DOCUMENT LIST

Patent Documents patent document 1: JP-A-2004-24852
patent document 2: JP-A-2005-229869
patent document 3: JP-A-2009-268433

Non-Patent Documents non-patent document 1: Aggarwal R K. Br J Ophthalmol 1997; 81:178-179.
non-patent document 2: Shimmura S. et al., Cornea 2005; 24(2):178-181.
non-patent document 3: Price F W Jr, Price M O. J Refract Surg. 2005; 21(4):339-345.
non-patent document 4: Yoshida S. et al., Stem Cells. 2006; 24(12):2714-2722.

SUMMARY OF THE INVENTION

Problems to be Solved by the Invention

It is an object of the present invention to provide a method of more efficiently producing corneal endothelial cells, more preferably stable production of a large amount of corneal endothelial cells by inducing more efficient differentiation of stem cells into corneal endothelial cells. Furthermore, the present invention aims to provide a medicament using corneal endothelial cells obtained by the method of the present invention.

Means of Solving the Problems

In view of the above-mentioned problems, the present inventors have conducted intensive studies and found that stem cells can be efficiently induced to differentiate into corneal endothelial cells by culturing the stem cells in a medium containing a particular differentiation inducer, and further, they have confirmed the function of the obtained corneal endothelial cell, which resulted in the completion of the present invention.

Accordingly, the present invention provides the following.

[1] A method of producing a corneal endothelial cell from a stem cell, comprising a step of cultivating the stem cell in a differentiation induction medium, wherein the differentiation induction medium comprises at least one kind selected from the group consisting of a GSK3 inhibitor (preferably a GSK3β inhibitor), retinoic acid, TGFb2, insulin and a ROCK inhibitor.

[1'] A method of producing a corneal endothelial cell from a stem cell, comprising a step of cultivating the stem cell in a differentiation induction medium, wherein the differentiation induction medium comprises a GSK3 inhibitor (preferably a GSK3β inhibitor) and retinoic acid.

[1"] The method of the above-mentioned [1'], wherein the differentiation induction medium further comprises at least one kind selected from the group consisting of TGFb2, insulin and a ROCK inhibitor.

[2] The method of the above-mentioned [1"], wherein the differentiation induction medium comprises a ROCK inhibitor, a GSK3 inhibitor (preferably a GSK3β inhibitor) and retinoic acid.

[3] The method of the above-mentioned [1], wherein the differentiation induction medium comprises retinoic acid, TGFb2 and a ROCK inhibitor.

[3'] The method of the above-mentioned [1"], wherein the differentiation induction medium comprises retinoic acid, TGFb2 and a ROCK inhibitor in an early stage of differentiation induction, and bFGF, a GSK3 inhibitor (preferably a GSK3β inhibitor) and a ROCK inhibitor in a late stage of differentiation induction.

[3"] The method of the above-mentioned [1"], wherein the differentiation induction medium comprises a ROCK inhibitor, a GSK3 inhibitor (preferably a GSK3β inhibitor) and retinoic acid in an early stage of differentiation induction, and a ROCK inhibitor in a late stage of differentiation induction.

[4] The method of the above-mentioned [1], wherein the differentiation induction medium comprises a GSK3 inhibitor (preferably a GSK3β inhibitor) and a ROCK inhibitor.

[5] The method of the above-mentioned [4], wherein the differentiation induction medium further comprises bFGF.

[6] The method of the above-mentioned [1"], wherein the differentiation induction medium comprises a GSK3 inhibitor (preferably a GSK3β inhibitor), retinoic acid, TGFb2, insulin and a ROCK inhibitor.

[7] The method of the above-mentioned [1] or [1"], wherein the GSK3 inhibitor is 6-bromoindirubin-3'-oxime (BIO).

[8] The method of the above-mentioned [1"], wherein the ROCK inhibitor is (+)-(R)-trans-4-(1-aminoethyl)-N-(4-pyridyl)cyclohexanecarboxamide dihydrochloride (Y-27632).

[9] The method of the above-mentioned [1] or [1"], wherein the retinoic acid is all-trans-retinoic acid.

[10] The method of the above-mentioned [1] or [1"], wherein the stem cell is an iPS cell-derived neural crest stem cell or a corneal stroma-derived neural crest stem cell.

[11] The method of the above-mentioned [10], wherein the stem cell is an iPS cell-derived neural crest stem cell.

[12] The method of the above-mentioned [11], further comprising a step of inducing a neural crest stem cell from an iPS cell.

[13] The method of the above-mentioned [1] or [1"], wherein the stem cell is a skin-derived pluripotent progenitor cell.

[A] The method of any one of the above-mentioned [1]-[13], [1'], [1"], [3'] and [3"], wherein the differentiation induction medium is a serum-free medium.

[14] A method of inducing differentiation of a corneal endothelial cell from a stem cell, comprising a step of cultivating the stem cell in a differentiation induction medium, wherein the differentiation induction medium comprises at least one kind selected from the group consisting of a GSK3 inhibitor (preferably a GSK3β inhibitor), retinoic acid, TGFb2, insulin and a ROCK inhibitor.

[14'] A method of inducing differentiation of a corneal endothelial cell from a stem cell, comprising a step of cultivating the stem cell in a differentiation induction medium, wherein the differentiation induction medium comprises a GSK3 inhibitor (preferably a GSK3β inhibitor) and retinoic acid.

[14"] The method of the above-mentioned [14], wherein the differentiation induction medium further comprises at least one kind selected from the group consisting of TGFb2, insulin and a ROCK inhibitor.

[15] The method of the above-mentioned [14"], wherein the differentiation induction medium comprises a ROCK inhibitor, a GSK3 inhibitor (preferably a GSK3β inhibitor) and retinoic acid.

[16] The method of the above-mentioned [14], wherein the differentiation induction medium comprises retinoic acid, TGFb2 and a ROCK inhibitor.

[16'] The method of the above-mentioned [14"], wherein the differentiation induction medium comprises retinoic acid, TGFb2 and a ROCK inhibitor in an early stage of differentiation induction, and bFGF, a GSK3 inhibitor (preferably a GSK3β inhibitor) and a ROCK inhibitor in a late stage of differentiation induction.

[16"] The method of the above-mentioned [14"], wherein the differentiation induction medium comprises a ROCK inhibitor, a GSK3 inhibitor (preferably a GSK3β inhibitor) and retinoic acid in an early stage of differentiation induction, and a ROCK inhibitor in a late stage of differentiation induction.

[17] The method of the above-mentioned [14], wherein the differentiation induction medium comprises a GSK3 inhibitor (preferably a GSK3β inhibitor) and a ROCK inhibitor.

[18] The method of the above-mentioned [17], wherein the differentiation induction medium further comprises bFGF.

[19] The method of the above-mentioned [14"], wherein the differentiation induction medium comprises a GSK3 inhibitor (preferably a GSK3β inhibitor), retinoic acid, TGFb2, insulin and a ROCK inhibitor.

[20] The method of the above-mentioned [14] or [14"], wherein the GSK3 inhibitor is 6-bromoindirubin-3'-oxime (BIO).

[21] The method of the above-mentioned [14"], wherein the ROCK inhibitor is (+)-(R)-trans-4-(1-aminoethyl)-N-(4-pyridyl)cyclohexanecarboxamide dihydrochloride (Y-27632).

[22] The method of the above-mentioned [14] or [14"], wherein the retinoic acid is all-trans-retinoic acid.

[23] The method of the above-mentioned [14] or [14"], wherein the stem cell is an iPS cell-derived neural crest stem cell or a corneal stroma-derived neural crest stem cell.

[24] The method of the above-mentioned [23], wherein the stem cell is an iPS cell-derived neural crest stem cell.

[25] The method of the above-mentioned [24], further comprising a step of inducing a neural crest stem cell from an iPS cell in vitro.

[26] The method of the above-mentioned [14] or [14"], wherein the stem cell is a skin-derived pluripotent progenitor cell.

[B] The method of any one of the above-mentioned [14]-[26], [14'], [14"], [16'] and [16"], wherein the differentiation induction medium is a serum-free medium.

[27] A medicament comprising the corneal endothelial cell obtained by the production method of any one of the above-mentioned [1]-[13], [1'], [1"], [3'], [3"] and [A].

[28] The medicament of the above-mentioned [27] for use for transplantation.

Effect of the Invention

According to the production method of the present invention, a corneal endothelial cell can be produced more efficiently from a stem cell. The corneal endothelial cell obtained by the production method can be used as a medicament for the treatment of a disease caused by functional disorder of corneal endothelial cell, such as a corneal sheet for corneal transplantation and the like, or for cellular therapy for treating such disease.

DESCRIPTION OF EMBODIMENTS

Figure 1:
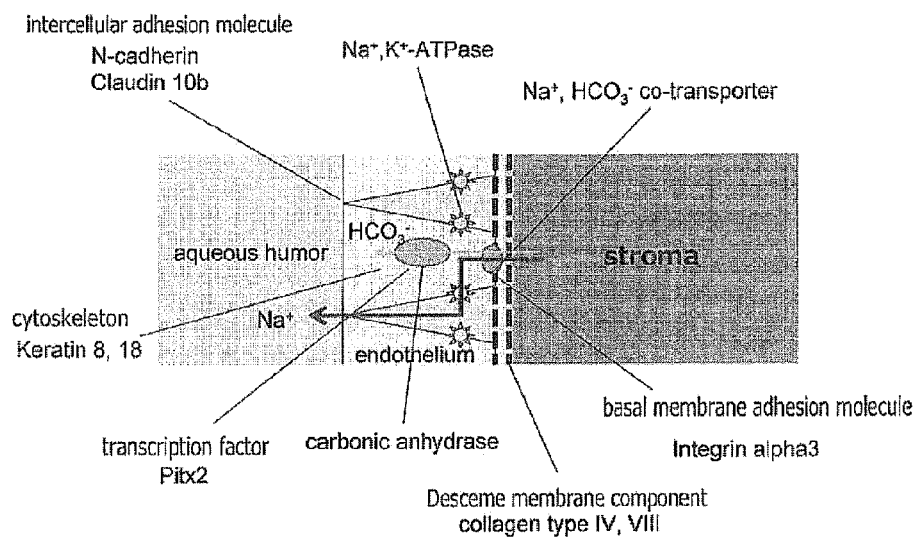
FIG. 1 schematically shows the relationship between corneal endothelial function and corneal endothelial cell marker.

The present invention is explained in the following. Unless particularly indicated, the terms used in the present specification have the meanings generally used in the pertinent field.

In the present invention, the "stem cell" means a cell capable of being cultured in vitro, and capable of differentiating into plural lines of cells constituting the body. Among others, it means a cell capable of differentiating into a corneal endothelial cell. Specific examples include embryonic stem cell (ES cell), fetal primordial germ cell-derived pluripotent stem cell (EG cell), testis-derived pluripotent stem cell (GS cell), somatic cell-derived artificial pluripotent stem cell (induced pluripotent stem cells; iPS cell), human somatic stem cell (tissue stem cell), and those capable of being induced to differentiate into a corneal endothelial cell. More preferred are an iPS cell-derived neural crest stem cell and a corneal stroma-derived neural crest stem cell. The neural crest stem cell is a pluripotent stem cell having a self-replication ability and multipotency, and is known to move from the back side of the neural tube into the whole body during the developmental process of vertebrata animals to contribute to the formation of various tissues. The corneal endothelium is considered to derive from neural crest, like corneal stroma.

As the ES cell, an ES cell derived from any warm-blooded animal, preferably a mammal, can be used. Examples of the mammal include mouse, rat, guinea pig, hamster, rabbit, cat, dog, sheep, swine, bovine, horse, goat, monkey, human and the like. A cell derived from human can be preferably used.

Specific examples of the ES cell include an ES cell of a mammal and the like, which is established by cultivating an early embryo before implantation, an ES cell established by cultivating an early embryo produced by nuclear transplantation of the nucleus of a somatic cell, and an ES cell wherein a gene on the chromosome of such ES cell is altered by a genetic engineering method. Each ES cell can be prepared by a method generally performed in the field, or according to known documents.

As the iPS cell, an iPS cell derived from any warm-blooded animal, preferably a mammal, can be used. Examples of the mammal include mouse, rat, guinea pig, hamster, rabbit, cat, dog, sheep, swine, bovine, horse, goat, monkey, human and the like. A cell derived from human can be preferably used.

Specific examples of the iPS cell include cells obtained by introducing plural genes into a somatic cell such as skin cell and the like, which have acquired multipotency same as that of ES cell. Examples thereof include iPS cell obtained by introducing Oct3/4 gene, Klf4 gene, C-Myc gene and Sox2 gene, iPS cell obtained by introducing Oct3/4 gene, Klf4 gene and Sox2 gene (Nat Biotechnol 2008; 26: 101-106) and the like. Furthermore, the production method of iPS cell has been intensively improved technically, for example, a method involving further reducing transgenes (Nature. 2008 Jul. 31; 454(7204): 646-50), a method utilizing a low-molecular-weight compound (Cell Stem Cell. 2009 Jan. 9; 4(1): 16-9, Cell Stem Cell. 2009 Nov. 6; 5(5): 491-503), a method utilizing a transcription factor protein instead of the gene (Cell Stem Cell. 2009 May 8; 4(5): 381-4) and the like. Since the basic property of the iPS cells produced, that is, having multipotency, is equivalent irrespective of the production methods, all of them can be used as the method of the present invention.

In the present invention, an iPS cell-derived neural crest stem cell is more preferably used. Using the neural crest stem cell, induction of differentiation into a corneal endothelial cell is facilitated. The neural crest stem cell can be induced from an iPS cell according to a method known in the field, or a method analogous thereto. For example, the induction can be performed according to the method described in Nature Protocols, 2010 vol. 5, No. 4, 688-701.

As the somatic stem cell, a somatic stem cell derived from human can be used. The somatic stem cell here is a cell capable of being differentiated into a corneal endothelial cell and, for example, corneal stroma-derived neural crest stem cell (COPs), mesenchymal stem cell (mesenchymal stem cells), skin-derived pluripotent progenitor cell (skin-derived precursors: SKPs) and the like can be mentioned. Preferred are COPs and SKPs. COPs can be prepared by, for example, the method described in non-patent document 4. Specifically, they are prepared by treating corneal stroma, obtained by removing epithelium and endothelium from mouse cornea, with collagenase, and culturing the separated cells in a DMEM/F12 medium added with EGF, FGF2, B27 supplement and LIF to give a cell population that form a spherical cell mass. SKPs can be prepared according to, for example, the method described in Nat Cell Biol., 2001 vol. 3, 778-784.

1. Production Method of Cell (Method for Induction of Cell Differentiation)

The production method of the present invention is a method of producing a corneal endothelial cell from a stem cell, and is also a method of inducing differentiation of a cell in a more undifferentiated state into a cell in a more differentiated state.

The present invention provides a method of producing a corneal endothelial cell, comprising a step of cultivating a stem cell in a medium containing at least one kind selected from the group consisting of a GSK3 inhibitor, retinoic acid, TGFb2, insulin and a ROCK inhibitor (hereinafter to be also referred to as the differentiation induction medium of the present invention), preferably a step of cultivating the cell in a differentiation induction medium essentially containing a GSK3 inhibitor and retinoic acid.

The stem cell to be used in this step is as mentioned above. It is preferably a cell destined to differentiate into a corneal endothelial cell, specifically an iPS cell-derived neural crest stem cell or a corneal stroma-derived neural crest stem cell (COPs). Use of a skin-derived pluripotent progenitor cell (SKPs) is also preferable. For example, when a more undifferentiated stem cell such as iPS cell, ES cell and the like is used, a step for induction into a neural crest stem cell can be or is preferably performed before the above-mentioned step. Such step can be performed by, for example, the method described in Nature Protocols, 2010, vol. 5, No. 4, 688-701 or a method analogous thereto.

GSK3 (glycogen synthase kinase 3), which is a serine/threonine protein kinase, is involved in many signal pathways relating to glycogen production, apoptosis, maintenance of stem cell and the like. GSK3 includes isoforms (GSK3α and GSK3β) encoded by different genes and having high homology at the amino acid level. In addition, it is known that GSK3β is also involved in Wnt signal, and inhibition of GSK3β activates Wnt signal. Examples of the GSK3 inhibitor include GSK3α inhibitor and GSK3β inhibitor. Specific examples of the GSK3 inhibitor include CHIR98014, CHIR99021, Kenpaullone, AR-AO144-18, TDZD-8, SB216763, BIO, TWS-119, SB415286, Ro3303544 and the like. All of these are commercially available, or can also be prepared by those of ordinary skill in the art, by reference to known documents. In this step, a GSK3β inhibitor is preferably used, and BIO (6-Bromoindirubin-3'-oxime) is particularly preferably used. The concentration of the GSK3 inhibitor in a medium is appropriately determined according to the kind of the inhibitor to be used. In the case of BIO, the concentration is generally 0.5-5 μM, preferably about 1 μM. One or more kinds of GSK3 inhibitors may be used in combination.

Examples of the retinoic acid to be used in this step include all-trans-retinoic acid, 9-cis-retinoic acid, 11-cis-retinoic acid, 13-cis-retinoic acid and the like. All of these are commercially available, or can also be prepared by those of ordinary skill in the art, by reference to known documents. In this step, it is preferably all-trans-retinoic acid. The concentration of the retinoic acid in a medium is appropriately determined according to the kind of the retinoic acid to be used. The concentration of all-trans-retinoic acid in a medium is generally 0.5-5 μM, preferably about 1 μM.

TGFb2 (transforming growth factor β2) is secreted as a latent protein, and is a member of a superfamily of disulfide-bound dimer proteins stored in the cell surface and extracellular substrate. TGFb2 is known to control proliferation, growth, differentiation and motility of cells, like, as is the case with the synthesis and deposition of extracellular substrate. The derivation of TGFb2 to be used in the present invention is not particularly limited as long as it is effective for differentiation induction into a corneal endothelial cell. In consideration of application to corneal transplantation, however, it is preferably derived from human. TGFb2 is commercially available, or can also be prepared by those of ordinary skill in the art, by reference to known documents. For example, TGFb2 can be synthesized based on known base sequences and amino acid sequences. The concentration of TGFb2 in a medium is generally 0.5-10 ng/ml, preferably about 1-5 ng/ml.

Insulin is a peptide hormone secreted by B cells in the pancreatic Langerhans' islet, and is known to bind to an insulin receptor in each tissue to exhibit a wide range of pharmacological actions such as promotion of glucose uptake, promotion of amino acid uptake, promotion of synthesis of protein, RNA and DNA, suppression of proteolysis and the like. It is also frequently used as an addition factor to a serum-free medium. The derivation of insulin to be used in the present invention is not particularly limited as long as it is effective for induction of differentiation into a corneal endothelial cell. In consideration of application to corneal transplantation, however, it is preferably derived from human. Insulin is commercially available, or can also be prepared by those of ordinary skill in the art, by reference to known documents. For example, it can be synthesized based on known base sequences or amino acid sequences. The concentration of insulin in a medium is generally 0.5-10 µM, preferably about 1 µM.

The ROCK inhibitor refers to a substance that inhibits the activity of Rho kinase. The Rho kinase is one kind of low-molecular-weight GTP binding protein (low molecular weight G protein) included in the category of GTPase, which is a degrading enzyme of GTP (guanosine triphosphate), and has a serine/threonine kinase region in the amino terminal, a coiled coil region in the center, and a Rho interaction region in the carboxy terminal.

Examples of the ROCK inhibitor to be used in this step include 1-(5-isoquinolinesulfonyl)-2-methylpiperazine (H-7), 1-(5-isoquinolinesulfonyl)-3-methylpiperazine (iso H-7), N-2-(methylamino)ethyl-5-isoquinolinesulfoneamide dihydrochloride (H-8), N-(2-aminoethyl)-5-isoquinolinesulfoneamide dihydrochloride (H-9), N-[2-(p-bromocinnamylamino)ethyl]-5-isoquinolinesulfoneamide dihydrochloride (H-89), N-(2-guanidinoethyl)-5-isoquinolinesulfoneamide hydrochloride (HA-1004), 1-(5-isoquinolinesulfonyl)homopiperazine dihydrochloride (Fasudil/HA-1077), (S)-(+)-2-methyl-4-glycyl-1-(4-methylisoquinolinyl-5-sulfonyl)homopiperidine dihydrochloride (H-1152), and (+)-(R)-trans-4-(1-aminoethyl)-N-(4-pyridyl)cyclohexanecarboxamide dihydrochloride (Y-27632). All of these are commercially available, and Y-27632 is particularly preferable. The concentration of the ROCK inhibitor in a medium is appropriately determined according to the kind of the inhibitor to be used. In the case of Y-27632, the concentration is generally 5-20 µM, preferably about 10 µM. One or more kinds of the ROCK inhibitors may be used in combination.

The above-mentioned GSK3 inhibitor, retinoic acid, TGFb2, insulin and ROCK inhibitor are generically referred to as the differentiation inducer of the present invention. In the present invention, at least one kind of the differentiation inducer is contained in a differentiation induction medium. Preferably, at least one kind selected from the group consisting of a GSK3 inhibitor, retinoic acid, insulin and a ROCK inhibitor is contained in a differentiation induction medium. More preferably, a GSK3 inhibitor and retinoic acid are contained in a differentiation induction medium. Further more preferably, a GSK3 inhibitor, retinoic acid and a ROCK inhibitor are contained in a differentiation induction medium. Particularly preferably, a differentiation induction medium containing all differentiation inducers of a GSK3 inhibitor, retinoic acid, TGFb2, insulin and a ROCK inhibitor is used.

It is also preferable to contain retinoic acid, TGFb2 and a ROCK inhibitor in a differentiation induction medium. It is also preferable to contain a GSK3 inhibitor and a ROCK inhibitor in a differentiation induction medium and, in this case, it is further more preferable to contain bFGF.

In this step, respective differentiation inducers may be simultaneously added to a medium, or may be separately added to a medium in a staggered manner as long as differentiation of a stem cell into a corneal endothelial cell can be induced. It is convenient and preferable to simultaneously add each differentiation inducer to a medium. Depending on the kind of the cell desired to be induced to differentiate, it is sometimes preferable to use differentiation induction media added with different differentiation inducers (or a combination thereof) for an early stage of differentiation induction (for example, day 0-2 of induction; or Day 0-4 of induction, which varies depending on the stem cell to be used), and a late stage (for example, at day 2 and the following of induction; or at day 4 and the following of induction, which varies depending on the stem cell to be used).

The medium to be used in this step is not particularly limited as long as it contains each differentiation inducer as mentioned above, and is generally a medium used for cultivating stem cells (hereinafter to be also referred to as a basal medium for convenience) and added with each differentiation inducer. The basal medium is not particularly limited as long as it can be used for culturing animal cells, and includes, for example, MEM medium, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, RPMI 1640 medium, Fischer's medium, and a mixed medium thereof. These media are commercially available. Furthermore, the medium to be used in this step can be a serum-containing medium or serum-free medium, preferably a serum-free medium. When the medium to be used in this step is a serum-containing medium, mammalian sera such as bovine serum, fetal bovine serum and the like can be used. The concentration of the serum in a medium is 0.1-20%, preferably 1-10%.

The basal medium to be used in this step is preferably MEM medium.

The medium to be used in this step may also contain a serum replacement. Examples of the serum replacement include albumin (e.g., lipid rich albumin), transferrin, fatty acid, collagen precursor, trace element (e.g., zinc, selenium and the like), growth factor (EGF, bFGF etc.), B-27 supplement, N2 supplement, knockout serum replacement, 2-mercaptoethanol or 3' thiolglycerol, equivalents thereof and the like. These serum replacements are also commercially available. Where necessary, the serum replacements can contain vitamin, buffering agent, inorganic salts, antibiotic (e.g., penicillin, streptomycin) and the like.

One preferable embodiment of the differentiation induction medium to be used in this step is a serum-containing medium containing a GSK3 inhibitor (preferably a GSK3β inhibitor), retinoic acid, TGFb2, insulin and a ROCK inhibitor as differentiation inducers.

In another preferable embodiment of the differentiation induction medium to be used in this step, a serum-containing medium containing retinoic acid, TGFb2 and a ROCK inhibitor as differentiation inducers is used for an early stage of differentiation induction (day 0-2 after differentiation induction), and a serum-containing medium containing a GSK3 inhibitor (preferably a GSK3β inhibitor), bFGF and a ROCK inhibitor as differentiation inducers is used for a late stage (at day 2 and the following of differentiation induction).

Another preferable embodiment of the differentiation induction medium to be used in this step is a serum-free medium containing retinoic acid, a GSK3 inhibitor (preferably a GSK3β inhibitor) and a ROCK inhibitor as differentiation inducers.

In another preferable embodiment of the differentiation induction medium to be used in this step, a serum-free medium containing retinoic acid, a GSK3 inhibitor (preferably a GSK3β inhibitor) and a ROCK inhibitor as differentiation inducers is used for an early stage of differentiation induction (day 0-4 after differentiation induction), and a serum-free medium containing a ROCK inhibitor as a differentiation inducer is used for a late stage (at day 4 and the following of differentiation induction).

This step is performed by culturing in a $CO_2$ incubator aerated with 1-10%, preferably 5%, carbon dioxide at a culture temperature suitable for culture of stem cells to be used, generally 30-40° C., preferably about 37° C., for a period sufficient for inducing differentiation into corneal endothelial cells. When iPS cell-derived neural crest stem cells, COPs or SKPs are used as the stem cell, they are preferably cultivated for 7-10 days. Where necessary, the medium is exchanged as appropriate (e.g., once every 3 days). As mentioned above, the kind (combination) of the differentiation inducers to be added can be or is preferably changed as necessary. When stem cells in a more undifferentiated state, that is, iPS cells, are used, a step of inducing differentiation of the iPS cells into neural crest stem cells is further performed (can be performed by, for example, the method described in Nature Protocols, 2010 vol. 5, No. 4, 688-701, or an improved method thereof) before the method of the present invention. However, this step generally takes about 1 month. Similarly, induction of differentiation of corneal stroma into COPs generally takes about 1 month (see non-patent document 4 and Examples for the detail of the step). Induction of differentiation into neural crest stem cells can be confirmed by measuring the expression of neural crest stem cell markers such as Twist1 (TWIST, DROSOPHILA, HOMOLOG OF, 1), Sox9 (SRY (sex determination region Y)-box9) and the like.

In this step, induction of differentiation of stem cells into corneal endothelial cells can be confirmed by evaluating the presence or absence of the expression of a protein necessary for exerting the function of corneal endothelial cells or a gene encoding same (corneal endothelial cell marker). The expression of the protein can be evaluated by a method utilizing an antigen antibody reaction and the like, and the expression of the gene can be evaluated by a method utilizing RT-PCR and the like. Examples of the marker include N-cadherin, $Na^+$, $K^+$-ATPase, $Na^+$, $HCO_3^-$-co-transporter, collagen type IV, collagen typeVIII, carbonic anhydrase, Keratin 8, Keratin 18, Paired-like homeodomain transcription factor 2, Integrin alpha 3, Claudin 10b and the like. The relationship between each marker and corneal endothelial function is schematically shown in FIG. 1.

In addition, confirmation that the stem cell has been induced to differentiate into corneal endothelial cell can be evaluated by measuring the $Na^+$, $K^+$-ATPase pumping function of the cell. The $Na^+$, $K^+$-ATPase pumping function of the cell can be measured, for example, according to the methods described in Investigative Ophthlmology & Visual Science, 2010 vol. 51, No. 8, 3935-3942, and Current Eye Research, 2009 vol. 34, 347-354 and using the Ussing chamber.

Conveniently, differentiation induction can also be confirmed by evaluating the cell morphology. A cell differentiated into an endothelial cell shows a mosaic growth form.

In the production method of the present invention, corneal endothelial cells can be supplied in large amounts by efficiently inducing stem cells to differentiate into corneal endothelial cells. The obtained corneal endothelial cells can be utilized as a medicament such as a corneal endothelial cell sheet for corneal transplantation and the like.

2. Medicament Containing Cells

The present invention provides a medicament containing corneal endothelial cells produced by the above-mentioned production method of the present invention (sometimes to be abbreviated in the present specification as the medicament of the present invention).

When a medicament containing corneal endothelial cells is produced as a corneal endothelial cell sheet, stem cells (preferably iPS cell-derived neural crest stem cells, corneal stroma-derived neural crest stem cells, skin-derived pluripotent progenitor cells) are plated on a culture substrate, and cultured in the differentiation induction medium of the present invention to induce differentiation into corneal endothelial cells on the culture substrate. While the culture substrate to be used in the present invention is not particularly limited as long as it is for cell culture, for example, naturally-occurring substance-derived polymer materials such as collagen, gelatin, cellulose, laminin and the like, synthetic polymer materials such as polystyrene, polyester, polycarbonate, poly(N-isopropylacrylamide) and the like, biodegradable polymer materials such as polylactic acid, polyglycolic acid and the like, hydroxyapatite, amniotic membrane and the like can be mentioned. Preferably, a culture substrate that does not cause rejection during transplantation is appropriately used according to the transplantation subject.

For transplantation, confluent corneal endothelial cells are used. For this end, the number of stem cells (preferably iPS cell-derived neural crest stem cells, corneal stroma-derived neural crest stem cells, skin-derived pluripotent progenitor cells) is generally set such that the cells are seeded at a cell density sufficient to form a cell sheet. Generally, the density of the cells to be seeded is $1.0\times10^4$-$5.0\times10^6$ cells/cm$^2$, more preferably $1.0\times10^5$-$1.0\times10^6$ cells/cm$^2$.

A corneal endothelial cell sheet obtained by the present invention can be used as a graft for the treatment of a disease requiring transplantation of corneal endothelium, for example, bullous keratopathy, corneal edema, corneal leukoma and the like.

In another embodiment other than a sheet, the obtained corneal endothelial cells as they are, a cell mass such as pellet obtained by concentration by filtration and the like, and the like are used as the medicament of the present invention. Moreover, it is also possible to add a protector such as glycerol, DMSO (dimethyl sulfoxide), propylene glycol, acetamide and the like to the medicament, and cryopreserve the mixture. For safer utilization of a medicament, the medicament may be subjected to a treatment under the conditions causing denaturation of pathological proteins, such as a heat treatment, a radiation treatment and the like, while retaining the function of the corneal endothelial cell.

EXAMPLES

The present invention is described in detail in the following by referring to Examples, which are not to be construed as limitative. Unless particularly specified, the reagents and materials to be used are commercially available.

Main abbreviations used in the present specification are each as follows.
(Abbreviation list)
iPS cell: induced pluripotent stem cell
COPs: Corneal-derived progenitors: corneal stroma-derived neural crest stem cell
SKPs: Skin-derived precursors: skin-derived pluripotent progenitor cell
GSK3: Glycogen synthase kinase 3
TGFb2: Transforming growth factor beta-2
EGF: Epidermal Growth Factor
FGF2: Fibroblast growth factor 2
bFGF: Basic fibroblast growth factor
LIF: Leukemia Inhibitory Factor
DMEM: Dulbecco's Modified Eagle's Medium
BME: Basal Medium Eagle
MEM: Minimum Essential Medium
IDMD: Iscove's Modified Dulbecco's Medium
RPMI: Roswell Park Memorial Institute medium
Atp1a1 (ATP1A1): $Na^+,K^+$-ATPase $\alpha$1-subunit
Slc4a4: $Na^+,HCO_3^-$-Co-transporter
Car2: Carbonic anhydrase
K8: Keratin 8
K18: Keratin 18
Col4a2: Collagen IV
Col8a2: Collagen VIII
Pitx2: Paired-like homeodomain transcription factor 2
Itga3: Integrin alpha 3
Cdh2: N-cadherin Cldn10b: Claudin 10b
Gapdh: Glyceraldehyde 3-phosphate dehydrogenase Example 1

Differentiation Induction of Mouse COPs into Corneal Endothelial Cells (Material and Method)
1. Separation of Mouse COPs Mouse COPs were separated from mouse cornea according to a publication (non-patent document 4). The corneal stromal disc was cut out from mouse (C57BL/6 mouse), processed into small pieces and digested with 0.05% trypsin (Sigma-Aldrich, St. Louis, Mo.) at 37° C. for 30 min. Then, they were treated with 78 U/ml collagenase (Sigma-Aldrich) and 38 U/ml hyaluronidase (Sigma-Aldrich) at 37° C. for 30 min. Parenchymal cells were mechanically dissociated to give single cells, and cultured in DMEM/F-12 (1:1) medium containing 20 ng/ml EGF (Sigma-Aldrich), ng/ml FGF2 (Sigma-Aldrich), B27 supplement (Invitrogen, Carlsbad, Calif.), and 103 U/ml LIF (Chemicon International, Temecula). The cells were cultured at plating density of $1 \times 10^5$ cells/ml under humidified atmosphere containing 5% $CO_2$ at 37° C. The first culture was performed in a 35 mm dish, and thereafter in a 25 $cm^2$ culture flask for 14-21 days. The formed sphere (spherical cell mass) was further cultured in a 75 $cm^2$ culture flask for 14-21 days. The medium was exchanged every 5-7 days. The dishes and flasks used for forming the sphere were made of polystyrene and without coating (Asahi Techno Glass (Tokyo, Japan)). COPs were obtained in this manner.

2. Preparation of Differentiation Induction Medium

As a basal medium, MEM medium (Sigma-Aldrich) was used, and 1% bovine serum and differentiation inducers were added. As the differentiation inducers, the following were used.
(i) BIO (GSK3 inhibitor) (concentration: 1 μM) available from: Calbiochem
(ii) all-trans-retinoic acid (concentration: 1 μM) available from: Sigma-Aldrich
(iii) TGFb2 (concentration: 5 ng/ml) available from: Peprotech
(iv) insulin (concentration: 1 μM) available from: Sigma-Aldrich
(v) Y-27632 (ROCK inhibitor) (concentration: 10 μM) available from: Nacalai Tesque (Results)

COPs separated from mouse corneal stroma were plated on a gelatin-coated 35 mm dish (Asahi Techno Glass) at a density of $1.0 \times 10^5$ cells/ml, and cultured in a differentiation induction medium at 37° C. for 7 days in the presence of 5% $CO_2$ to induce differentiation. The obtained cells were observed under a phase contrast microscope to find that COPs in the state of a cell mass came to show a mosaic growth form very similar to endothelial cells.

Example 2

Differentiation Induction of Human iPS Cell-Derived Neural Crest Stem Cell into Corneal Endothelial Cell—(1)

(Material and Method)
1. Preparation of Human iPS Cell-Derived Neural Crest Stem Cell Based on a publication (Nature Protocols, 2010 vol. 5, No. 4, 688-701), neural crest stem cells were obtained from human iPS cell. This Example is different from the above-mentioned publication in that floating culture was employed without using Matrigel for culturing iPS cells. Suspension culture enabled more efficient induction of differentiation into neural crest stem cells. The human iPS cells used were 201B7 (provided by Prof. Shinya Yamanaka (Kyoto University) and Prof. Hideyuki Okano (Keio University)).

2. Preparation of Differentiation Induction Medium

The medium was prepared in the same manner as the differentiation induction medium used in Example 1.

(Results)

Human iPS cell-derived neural crest stem cells were plated in a gelatin-coated 35 mm dish (Asahi Techno Glass) at a density of $1.0 \times 10^5$ cells/ml, and cultured in a differentiation induction medium at 37° C. for 7 days in the presence of 5% $CO_2$ to induce differentiation. The obtained cells were observed under a phase contrast microscope to find that the cells cultured in the differentiation induction medium came to show a mosaic growth form very similar to endothelial cells.

Example 3

Evaluation of Corneal Endothelial Cell (Corneal Endothelial Cell Marker Measurement)

Using corneal endothelial cells obtained by inducing differentiation of COPs, which were prepared in the same manner as in Example 1, and corneal endothelial cells obtained by inducing differentiation of human iPS cell-derived neural crest stem cells, which were obtained in the same manner as in Example 2, the expression state of corneal endothelial cell marker was examined by RT-PCR method. The primers used are shown in Table 1 (for mouse) and Table 2 (for human).

TABLE 1 for mouse COPs

| Gene | Forward sequence (5'-3') | Reverse sequence (3'-5') | product size |
|---|---|---|---|
| Atp1a1 | CCATCGCTTACACCCTA ACC (SEQ ID NO: 1) | TCTTGCAGATGACCAAG TCG (SEQ ID NO: 2) | 492 |
| Slc4a4 | TCTTCCTGGGCACTTAC ACC (SEQ ID NO: 3) | AGGAGCATACCACCATG AGG (SEQ ID NO: 4) | 408 |
| Car2 | GATCCTTGCTCCCTTCT TCC (SEQ ID NO: 5) | ATCACCCAGCCTAACTG TGC (SEQ ID NO: 6) | 326 |
| Col4a2 | TGGAGTTCCTGGTTTGA AGG (SEQ ID NO: 7) | TCACCAAAGTCCCCAGT AGG (SEQ ID NO: 8) | 420 |
| Col8a2 | GGTCCAGTAGGGGCTAA AGG (SEQ ID NO: 9) | CCTGTAAAACCTGGCTC ACC (SEQ ID NO: 10) | 422 |
| Cdh2 | CAGGAAAAGTGGCAGGT AGC (SEQ ID NO: 11) | ATAATGAAGATGCCCGT TGG (SEQ ID NO: 12) | 302 |
| Gapdh | GACCACAGTCCATGCCAT CAC (SEQ ID NO: 13) | AGACAACCTGGTCCTCA GTGTAGC (SEQ ID NO: 14) | 459 |

TABLE 2 for human iPS cell

| Gene | Forward sequence (5'-3') | Reverse sequence (3'-5') | product size |
|---|---|---|---|
| Atp1a1 | CTACCTGGCTTGCTCTG TCC (SEQ ID NO: 15) | CGTCTTTCAGCTCCTCATCC (SEQ ID NO: 16) | 363 |

TABLE 2-continued for human iPS cell

| Gene | Forward sequence (5'-3') | Reverse sequence (3'-5') | product size |
|---|---|---|---|
| Slc4a4 | TGTGCCAAGTGAGTTCA AGC (SEQ ID NO: 17) | ACTGTCGATGTGAGCAATGG (SEQ ID NO: 18) | 301 |
| Car2 | CAATGGTCATGCTTTCA ACG (SEQ ID NO: 19) | CAATCCAGGTCACACATTCC (SEQ ID NO: 20) | 446 |
| Col4a2 | TGCATGAAGAACCTGTG AGC (SEQ ID NO: 21) | TGCTGTTGTCTCGTCTGTCC (SEQ ID NO: 22) | 392 |
| Col8a2 | ACCCTCTGGTTCCAATT TCC (SEQ ID NO: 23) | TCAGCCAGTCAGAAGTCAGC (SEQ ID NO: 24) | 433 |
| Cdh2 | AGGTTTGCCAGTGTGAC TCC (SEQ ID NO: 25) | ATGGGTCTTTCATCCATTCG (SEQ ID NO: 26) | 346 |
| Gapdh | GTCAAGGCTGAGAACGG GAA (SEQ ID NO: 27) | GCTTCACCACCTTCTTGATG (SEQ ID NO: 28) | 613 |

Figure 2:
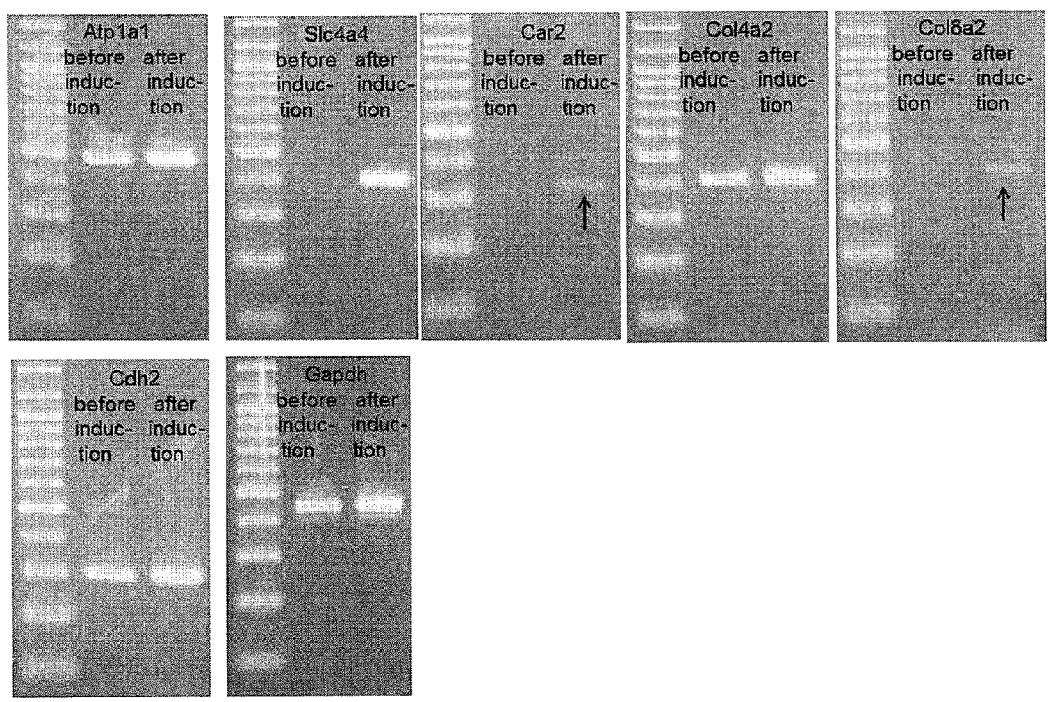
FIG. 2 shows the comparison results of the expression of corneal endothelial cell marker before and after differentiation induction of mouse corneal stroma-derived neural crest stem cells (COPs), which confirm expression of all markers after induction.

The comparison results of the expression of the corneal endothelial cell marker in COPs before and after differentiation induction are shown in FIG. 2.

Figure 3:
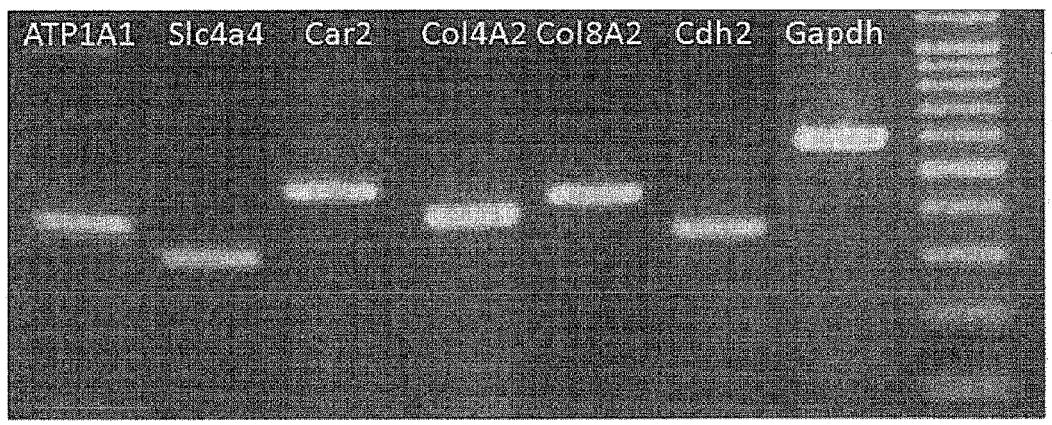
FIG. 3 shows the examination results of the expression of corneal endothelial cell markers after differentiation induction of human iPS cell-derived neural crest stem cell, which confirm expression of all markers after induction.

The measurement results of the expression of the corneal endothelial cell marker in human iPS cell-derived neural crest stem cells after differentiation induction are shown in FIG. 3.

It is appreciated that, in both of them, all markers were expressed after differentiation induction.

Example 4

Evaluation of Corneal Endothelial Cell (Na, K-ATPase Pumping Function Measurement)

Using corneal endothelial cells obtained by inducing differentiation of COPs, which were obtained in Example 1, and corneal endothelial cells obtained by inducing differentiation of human iPS cell-derived neural crest stem cells, which were obtained in Example 2, the Na, K-ATPase pumping function was measured.

As controls, cultured mouse corneal endothelial cells, 3T3 cells, COPs before differentiation induction, and COPs cultured in a medium containing only one kind of differentiation inducer (TGFb2 or a GSK3 inhibitor) were measured for the pumping function.

Figure 4:
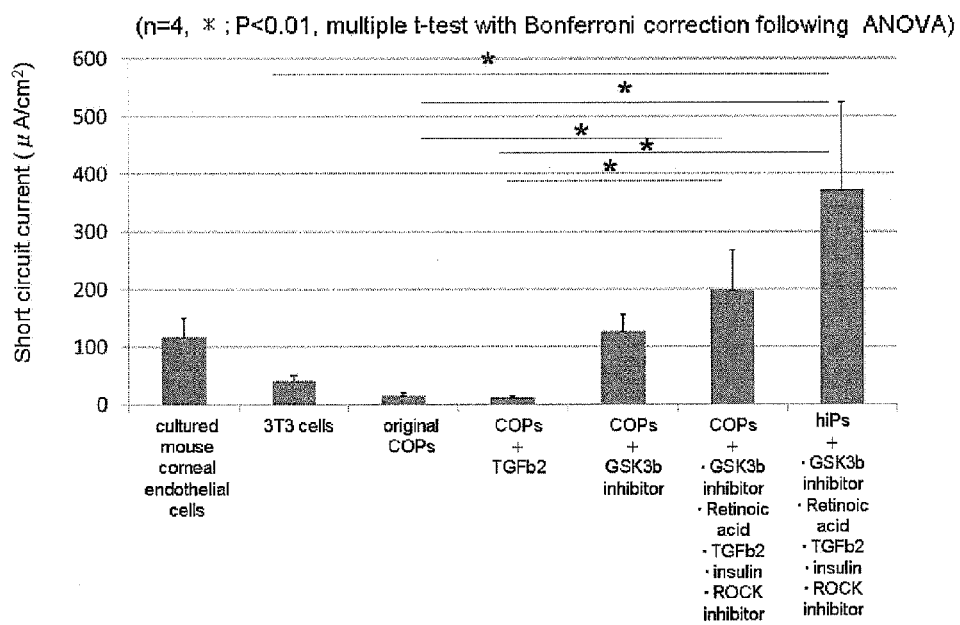
FIG. 4 shows the measurement results of the pumping function of human iPS cell-derived neural crest stem cell-induced cell, mouse COPs-induced cell, mouse corneal endothelial cell, and 3T3 cell, wherein remarkable expression of pumping function was confirmed in human iPS cell-derived and neural crest stem cell-induced cell, and mouse COPs-induced cell cultured in a medium added with one or more kinds of differentiation inducers.

Respective cells were allowed to become confluent on a dedicated polyester transwell (Corning Incorporated), and inserted into Ussing chamber (Physiological Instrument; EM-CSYS-2). The short circuit currents (SCC) of the front and back of the wells were measured, and Na, K-ATPase pumping function was quantified from the difference in SCC before and after addition of 10 μM ouabain. The results are shown in FIG. 4.

It was shown that the corneal endothelial cells obtained using the differentiation induction medium of the present invention have a superior pumping function.

Example 5

Corneal Transplantation Test (Preparation)
COPs or human iPS cell-derived neural crest stem cells were labeled with fluorescence dye PKH26 (red) (Sigma-Aldrich), and cultured on a gelatin-coated type 1-collagen sheet in a differentiation induction medium, which is similar to that prepared in Example 1, at 37° C. for 7 days in the presence of 5% $CO_2$ to give a confluent cell sheet (I).

(Procedure)
1. Anterior chamber is formed with hyaluronic acid.
2. Rabbit cornea is punched out with a 7.0 mm trephine.
3. Purchased host cornea (Funakoshi Cororation) is punched out with a 8.0 mm punch, and Descemet's membrane is detached with a tweezer (II).
4. The cell sheet (I) is punched out with a 8.0 mm punch, placed on the back surface of cornea (II). Water is absorbed with MQA sponge, and the membrane is naturally dried for several seconds (III).
5. (III) is placed back on the original rabbit cornea and sutured with 10-0 nylon.

(Measurement)
The corneal thickness was measured by a corneal thickness measuring apparatus (TOMEY CORPORATION; SP-100), and the intraocular pressure was measured by an intraocular pressure measuring apparatus (White Medical Co., Ltd.; AccuPen (manufactured by ACCUTOME)).

Figure 5:
FIG. 5 shows the outcome of transplantation of corneal endothelial cells, which were obtained by inducing differentiation of mouse COPs, to rabbit cornea. In the eye after the transplantation, corneal edema caused by endothelial functional disorder was improved, and further, an improving effect was also confirmed in the corneal thickness.
Figure 5:
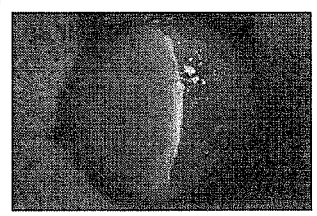
Figure 5:
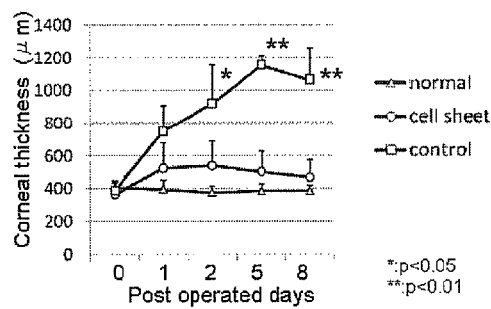
Figure 5:
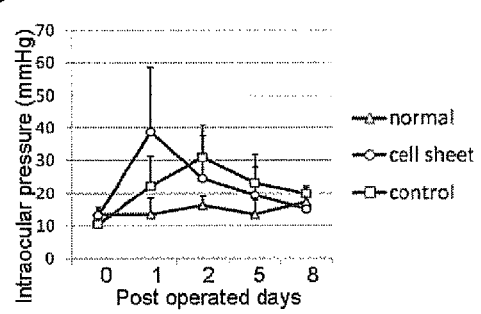
Figure 6:
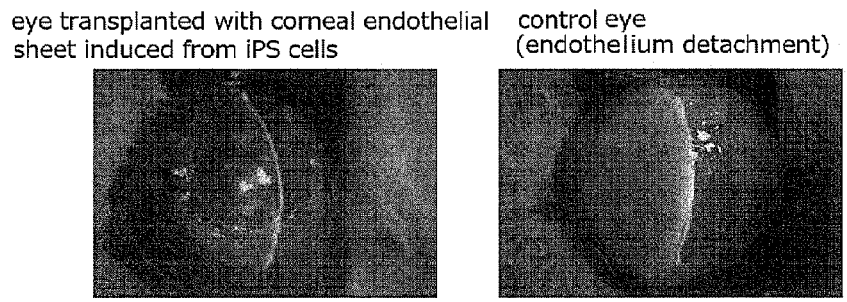
FIG. 6 shows the outcome of transplantation of corneal endothelial cells, which were obtained by inducing differentiation of human iPS cell-derived neural crest stem cell, to rabbit cornea. In the eye after the transplantation, corneal edema caused by endothelial functional disorder was improved, and further, an improving effect was also confirmed in the corneal thickness.
Figure 6:
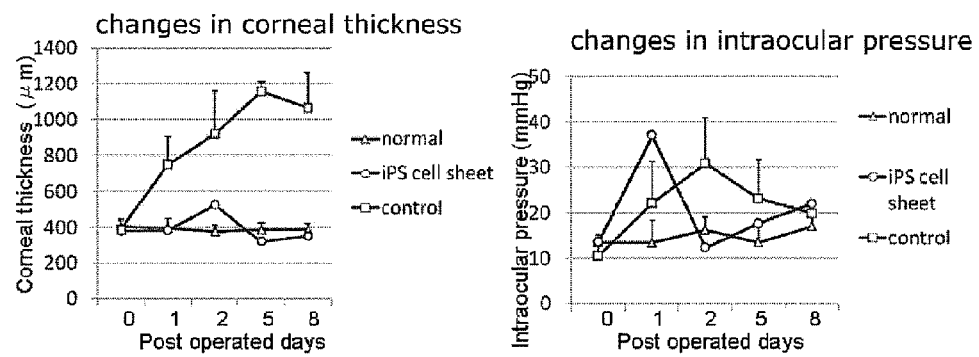

(Results)
The rabbit eye transplanted with the corneal endothelial cell sheet obtained by inducing differentiation of COPs is shown in FIG. 5, and the rabbit eye transplanted with the corneal endothelial cell sheet obtained by inducing differentiation of human iPS cells is shown in FIG. 6. Since both corneal endothelial sheets were transplanted, corneal edema caused by endothelial functional disorder was improved, and further, an improving effect on the corneal thickness was observed.

Example 6

Differentiation Induction of Human COPs into Corneal Endothelial Cells (Material and Method)
1. Separation of Human COPs
COPs were obtained from human by partially altering Example 1. To be specific, corneal stroma obtained by removing epithelium and endothelium from human cornea was treated with collagenase, and separated cells were cultured in DMEM/F12 medium added with EGF, FGF2, B27 supplement, N2 supplement and heparin to give a cell population forming a spherical cell mass, whereby COPs were prepared.

2. Preparation of Differentiation Induction Medium
As a basal medium, MEM medium (Sigma-Aldrich) was used, and 1% bovine serum and differentiation inducers were added. As the differentiation inducers, the following were used.

(differentiation induction medium A: differentiation induction day 0-2)
(i) all-trans-retinoic acid (concentration: 1 μM) available from: Sigma-Aldrich
(ii) TGFb2 (concentration: 1 ng/ml) available from: Peprotech
(iii) Y-27632 (ROCK inhibitor) (concentration: 10 μM) available from: Nacalai Tesque (differentiation induction medium B: at day 2 and the following of differentiation induction)
(i) BIO (GSK3 inhibitor) (concentration: 1 μM) available from: Calbiochem
(ii) bFGF (concentration: 40 ng/ml) available from: Sigma Aldrich (iii) Y-27632 (ROCK inhibitor) (concentration: 10 μM) available from: Nacalai Tesque (Results)

Figure 7:
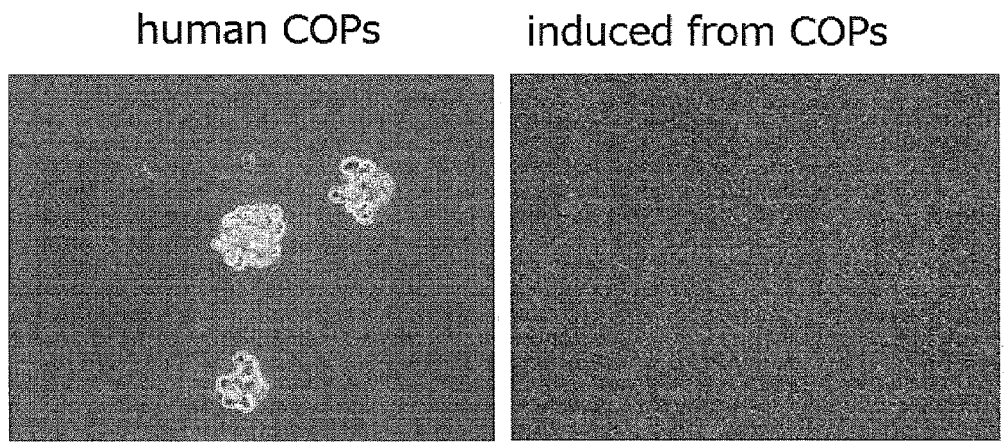
FIG. 7 is a microscopic photograph of a corneal endothelial cell sheet obtained by inducing differentiation of human COPs.
Figure 8:
FIG. 8 shows the outcome of transplantation of corneal endothelial cells, which were obtained by inducing differentiation of human COPs, to rabbit cornea. In the eye after the transplantation, corneal edema caused by endothelial functional disorder was improved, and further, an improving effect was also confirmed in the corneal thickness.
Figure 8:
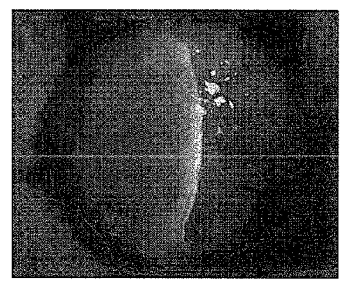
Figure 8:
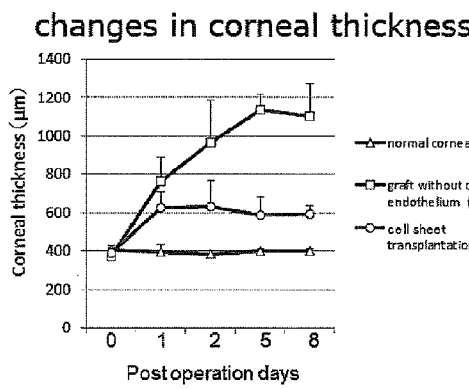
Figure 8:
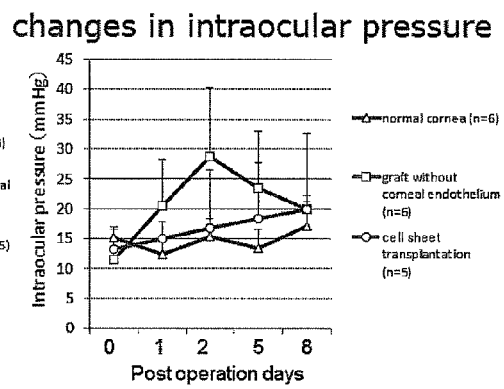

In the same manner as in Example 5, a confluent cell sheet was produced by culturing COPs separated from human cornea on a gelatin-coated type 1-collagen sheet in a differentiation induction medium at 37° C. for 7 days in the presence of 5% $CO_2$ (cultured in differentiation induction medium A for 0-2 days and, after day 2, in replaced differentiation induction medium B on the same sheet) (FIG. 7). A corneal endothelial sheet obtained by inducing differentiation of human COPs was transplanted into rabbit cornea in the same manner as in Example 5. Since the corneal endothelial sheet was transplanted, corneal edema caused by endothelial functional disorder was improved, and further, an improving effect on the corneal thickness was observed (FIG. 8).

Example 7

Differentiation Induction of Mouse SKPs into Corneal Endothelial Cells (Material and Method)
1. Separation of Mouse SKPs SKPs were obtained from the mouse skin according to a publication (Nat Cell Biol., 2001 vol. 3, 778-784).

2. Preparation of differentiation induction medium

A differentiation induction medium was prepared in the same manner as in Example 1.

(Results)

Figure 9:
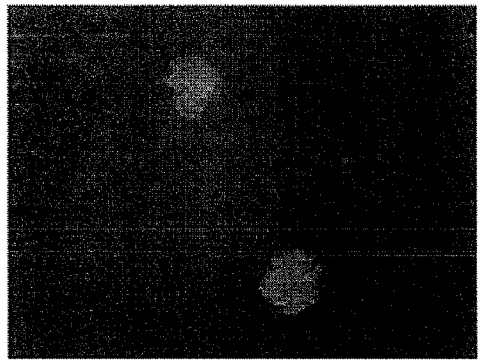
FIG. 9 is a microscopic photograph of a corneal endothelial cell sheet obtained by inducing differentiation of mouse SKPs.
Figure 9:
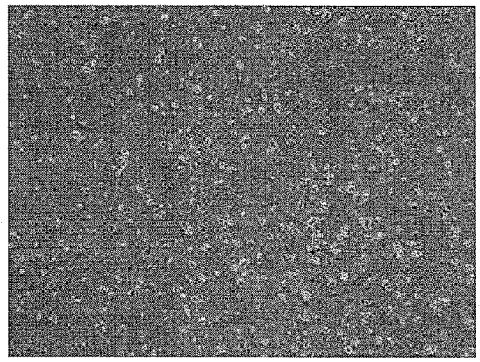

In the same manner as in Example 5, SKPs separated from the mouse skin were labeled with fluorescence dye PKH26 (red) (Sigma-Aldrich), and cultured on a gelatin-coated type 1-collagen sheet in a differentiation induction medium at 37° C. for 7 days in the presence of 5% $CO_2$ to give a confluent cell sheet (FIG. 9).

Figure 10:
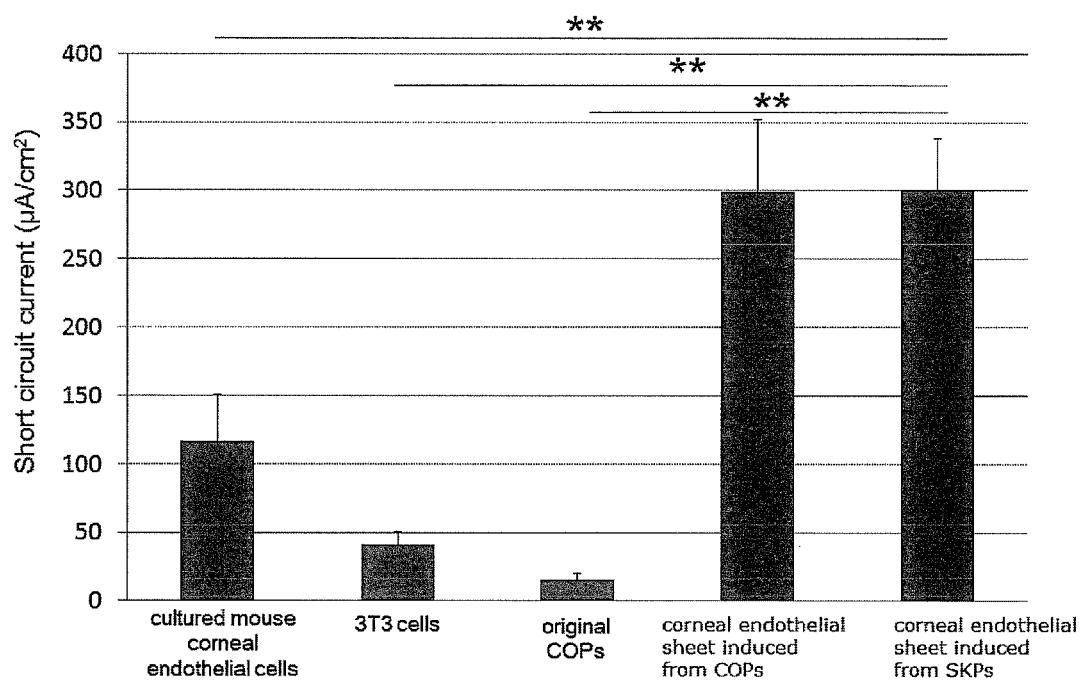
FIG. 10 shows the measurement results of the pumping function of corneal endothelial cell induced from mouse SKPs, cultured mouse corneal endothelial cells, 3T3 cells, mouse COPs, and corneal endothelial cells induced from mouse COPs.

Using the obtained corneal endothelial sheet obtained by inducing differentiation of SKPs, the Na, K-ATPase pumping function was measured in the same manner as in Example 4. As controls, cultured mouse corneal endothelial cells, 3T3 cells, mouse COPs before differentiation induction, and a corneal endothelial sheet obtained by inducing differentiation of mouse COPs prepared in Example 5 were measured for the pumping function. The results are shown in FIG. 10.

The corneal endothelial cells obtained using the differentiation induction medium of the present invention were shown to have a superior pumping function.

Figure 11:
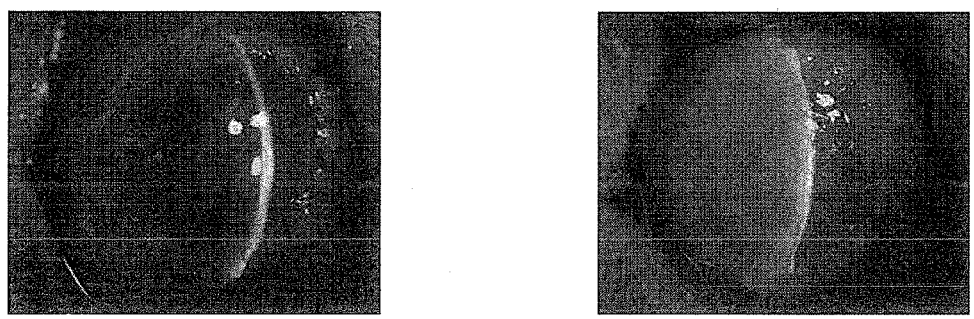
FIG. 11 shows the outcome of transplantation of corneal endothelial cells, which were obtained by inducing differentiation of mouse SKPs, to rabbit cornea. In the eye after the transplantation, corneal edema caused by endothelial functional disorder was improved, and further, an improving effect was also confirmed in the corneal thickness.
Figure 11:
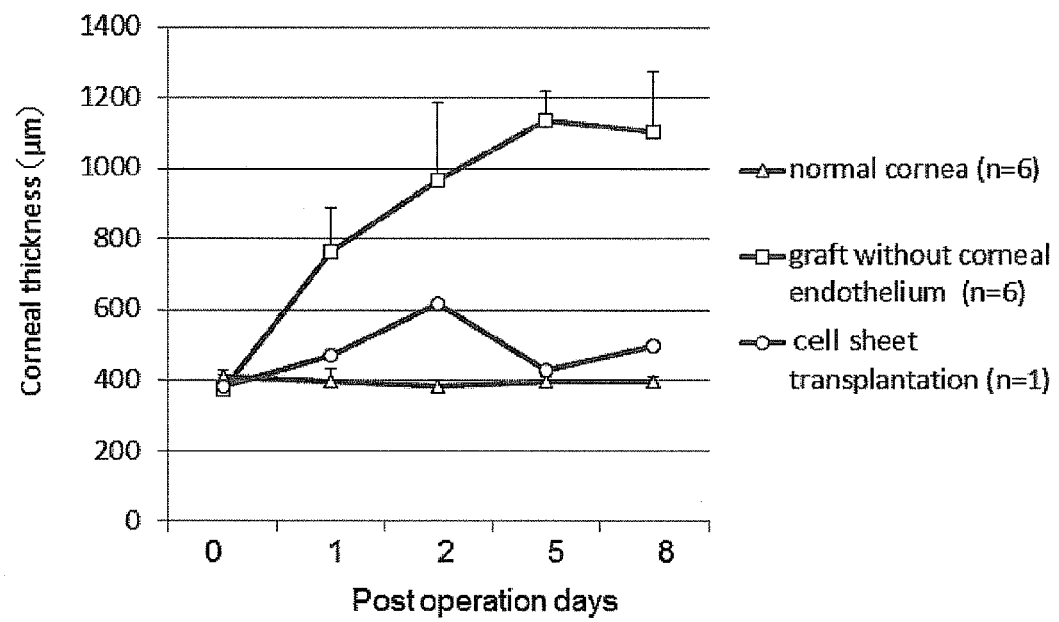

Furthermore, a corneal endothelial sheet obtained by inducing differentiation of mouse SKPs was transplanted into rabbit cornea in the same manner as in Example 5. Since the corneal endothelial sheet was transplanted, corneal edema caused by endothelial functional disorder was improved, and further, an improving effect on the corneal thickness was observed (FIG. 11).

Example 8

Differentiation Induction of Human iPS Cell-Derived Neural Crest Stem Cell into Corneal Endothelial Cell—(2)

Using the corneal endothelial cells obtained by inducing differentiation of human iPS cell-derived neural crest stem cells, which were obtained in the same manner as in Example 2, the expression state of corneal endothelial cell marker was examined by RT-PCR method. The primers used are shown in Table 3.

TABLE 3

| Gene | Forward sequence (5'-3') | Reverse sequence (3'-5') | product size |
|---|---|---|---|
| Atp1a1 | CCAAAGACAGGGTGCTAT CG (SEQ ID NO: 29) | TTGCTTGGACACATCT GAGC (SEQ ID NO: 30) | 118 |
| Slc4a4 | TGTGCCAAGTGAGTTCAA GC (SEQ ID NO: 31) | ACTGTCGATGTGAGCA ATGG (SEQ ID NO: 32) | 119 |
| Car2 | GATGGAGGATGAAGCTGT CC (SEQ ID NO: 33) | TGTAACTCTTCGGCAC ATGG (SEQ ID NO: 34) | 149 |
| K8 | GGAAGCTGGTGTCTGAGT CC (SEQ ID NO: 35) | CTCCTGTTCCCAGTGC TACC (SEQ ID NO: 36) | 134 |
| K18 | GGAGCACTTGGAGAAGAA GG (SEQ ID NO: 37) | AAGTCATCAGCAGCAA GACG (SEQ ID NO: 38) | 153 |
| Col4a2 | ACGAGACAACAGCACACA GG (SEQ ID NO: 39) | CGGTATTTGGGAGAAC ATGG (SEQ ID NO: 40) | 152 |
| Col8a2 | CAAGAGGGGTTCATCTGT GG (SEQ ID NO: 41) | GTCCAGAGCCAACTCA TTCC (SEQ ID NO: 42) | 144 |
| Cdh2 | TGACAACATTCACTGCTC AGG (SEQ ID NO: 43) | GATTCTCGGTCCAAAA CAGC (SEQ ID NO: 44) | 142 |
| Cldn10b | ACGGCACGGTCATCACAA CC (SEQ ID NO: 45) | GACAGCAGCGATCATA AGTCC (SEQ ID NO: 46) | 155 |
| Itga3 | GGTGCCTACAACTGGAAA GG (SEQ ID NO: 47) | GCCTACCTGCATCGTG TACC (SEQ ID NO: 48) | 126 |
| Pitx2 | GATGTGCCAAAGGTCAGA GG (SEQ ID NO: 49) | ATTGCACGGGATAGAA GTGG (SEQ ID NO: 50) | 160 |
| Gapdh | AACGGATTTGGTCGTATT GG (SEQ ID NO: 51) | CATGGGTGGAATCATA TTGG (SEQ ID NO: 52) | 136 |

In this Example, MEM medium (Sigma-Aldrich) was used as a basal medium, and a serum-free medium added with differentiation inducers was used as a differentiation induction medium. As the differentiation inducers, the following were used.

Figure 12:
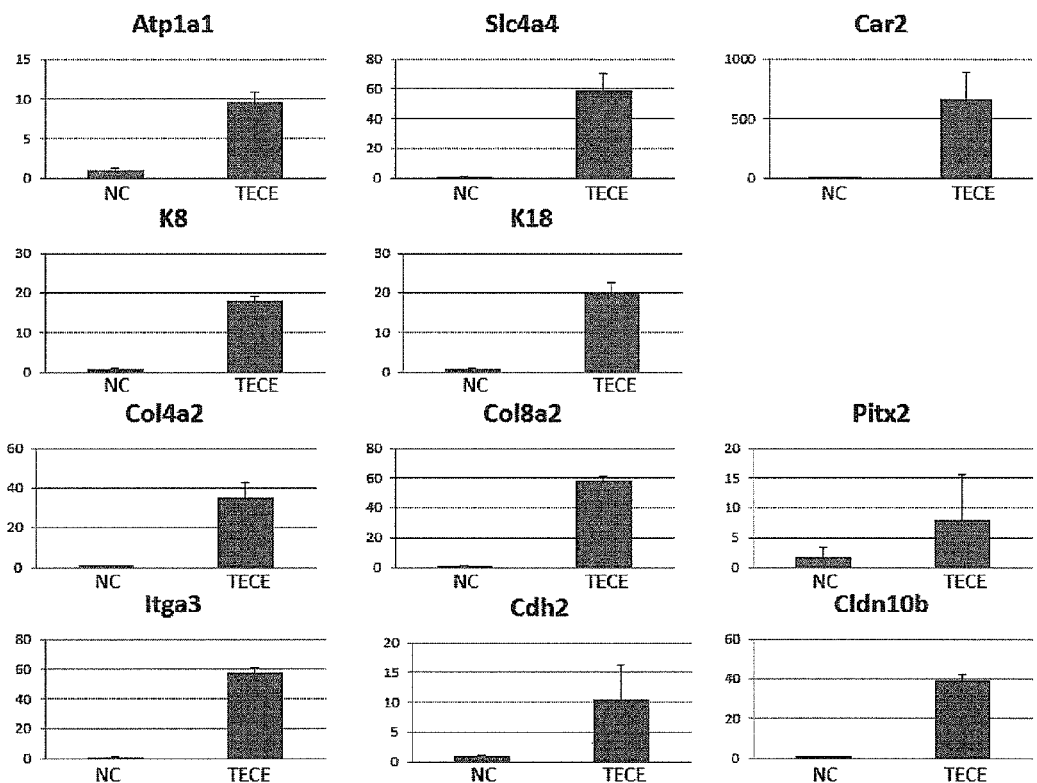
FIG. 12 shows the examination results of the expression of corneal endothelial cell markers after differentiation induction of human iPS cell-derived neural crest stem cell, which confirm expression of all markers after induction.

(i) BIO (GSK3 inhibitor) (concentration: 1 μM) available from: Calbiochem
(ii) all-trans-retinoic acid (concentration: 1 μM) available from: Sigma-Aldrich
(iii) Y-27632 (ROCK inhibitor) (concentration: 10 μM) available from: Nacalai Tesque The results are shown in FIG. 12. It is appreciated that, in both of them, all markers were expressed after differentiation induction.

Example 9

Differentiation Induction of Human iPS Cell-Derived Neural Crest Stem Cell into Corneal Endothelial Cell—(3)

(Material and Method)
1. Human iPS Cell-Derived Neural Crest Stem Cell

Human iPS cell-derived neural crest stem cells were prepared in the same manner as in Example 2.

2. Preparation of Differentiation Induction Medium

As a basal medium, MEM medium (Sigma-Aldrich) was used, and differentiation inducers were added. Serum was not added (serum-free medium). As the differentiation inducers, the following were used.

(differentiation induction medium A: differentiation induction Day 0-4)
(i) all-trans-retinoic acid (concentration: 1 μM) available from: Sigma-Aldrich
(ii) BIO (GSK3 inhibitor) (concentration: 1 μM) available from: Calbiochem
(iii) Y-27632 (ROCK inhibitor) (concentration: 10 μM) available from: Nacalai Tesque
(differentiation induction medium B: at day 4 and the following of differentiation induction)
(i) Y-27632 (ROCK inhibitor) (concentration: 10 μM) available from: Nacalai Tesque
(Results)

Figure 13:
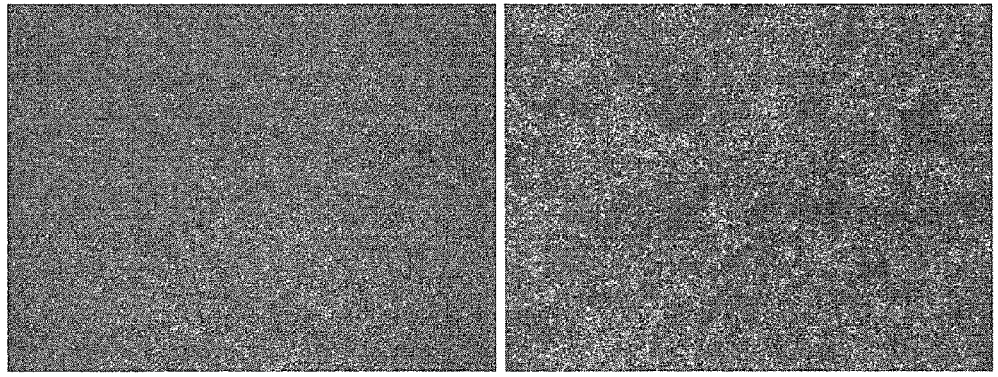
FIG. 13 is a microscopic photograph of a corneal endothelial cell sheet obtained by inducing differentiation of human iPS cell-derived neural crest stem cell in a serum-free differentiation induction medium by using collagen vitrigel as a carrier.

Human iPS cell-derived neural crest stem cells prepared in the same manner as in Example 2 were cultured in a differentiation induction medium on a fibronectin-coated type 1-collagen sheet at 37° C. for 2 days in the presence of 5% $CO_2$, and the cells were once collected. The collected cells were plated on Collagen vitrigel coated with gelatin and laminin in differentiation induction medium A ($5.0 \times 10^5$ cells/$cm^2$), and cultured at 37° C. for 2 days in the presence of 5% $CO_2$. The medium was exchanged with differentiation induction medium B, and the cells were further cultured at 37° C. for 3 days in the presence of 5% $CO_2$ to give a confluent cell sheet (FIG. 13).

INDUSTRIAL APPLICABILITY

According to the production method of the present invention, corneal endothelial cells can be produced more efficiently from stem cells. The corneal endothelial cells obtained by the production method can be used as a medicament for the treatment of diseases caused by functional disorder of corneal endothelial cells, such as corneal sheet for corneal transplantation and the like, and for cell therapy for the treatment of such diseases.

This application is based on patent application Nos. 2011-222138 (filing date Oct. 6, 2011) and 2012-076080 (filing date Mar. 29, 2012) filed in Japan, the contents of which are incorporated in full herein.

The invention claimed is:

1. A method of producing a corneal endothelial cell from a human iPS cell-derived neural crest stem cell, comprising a step of cultivating the stem cell in a differentiation induction medium, wherein the differentiation induction medium is a serum-containing medium comprising a glycogen synthase kinase 3 (GSK3) inhibitor, retinoic acid, transforming growth factor (TGFb2), insulin, and a Rho-associated protein kinase (ROCK) inhibitor.

2. A method of producing a corneal endothelial cell from a human iPS cell-derived neural crest stem cell, comprising a step of cultivating the stem cell in a differentiation induction medium, wherein the differentiation induction medium is a serum-free medium comprising a Rho-associated protein kinase (ROCK) inhibitor, a glycogen synthase kinase 3 (GSK3) inhibitor and retinoic acid in an early stage of differentiation induction, and a ROCK inhibitor in a late stage of differentiation induction.

3. The method according to claim 1, wherein the GSK3 inhibitor is 6-bromoindirubin-3'-oxime (BIO).

4. The method according to claim 1, wherein the ROCK inhibitor is (+)-(R)-trans-4-(1-aminoethyl)-N-(4-pyridyl)cyclohexanecarboxamide dihydrochloride (Y-27632).

5. The method according to claim 1, wherein the retinoic acid is all-trans-retinoic acid.

6. The method according to claim 2, wherein the GSK3 inhibitor is 6-bromoindirubin-3'-oxime (BIO).

7. The method according to claim 2, wherein the retinoic acid is all-trans-retinoic acid.

8. The method according to claim 2, wherein the ROCK inhibitor is (+)-(R)-trans-4-(1-aminoethyl)-N-(4-pyridyl)cyclohexanecarboxamide dihydrochloride (Y-27632).

9. The method according to claim 8, wherein the GSK3 inhibitor is 6-bromoindirubin-3'-oxime (BIO).

10. The method according to claim 8, wherein the retinoic acid is all-trans-retinoic acid.

11. The method according to claim 10, wherein the GSK3 inhibitor is 6-bromoindirubin-3'-oxime (BIO).

12. The method according to claim 6, wherein the retinoic acid is all-trans-retinoic acid.

13. The method according to claim 4, wherein the GSK3 inhibitor is 6-bromoindirubin-3'-oxime (BIO).

14. The method according to claim 4, wherein the retinoic acid is all-trans-retinoic acid.

15. The method according to claim 14, wherein the GSK3 inhibitor is 6-bromoindirubin-3'-oxime (BIO).

16. The method according to claim 3, wherein the retinoic acid is all-trans-retinoic acid.

* * * * *

SEQUENCE LISTING

```
<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Synthetic Forward Primer for Atp1a1 (mouse)

<400> SEQUENCE: 1
ccatcgctta caccctaacc                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Reverse Primer for Atp1a1 (mouse)

<400> SEQUENCE: 2
tcttgcagat gaccaagtcg                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic Forward Primer for Slc4a4 (mouse)

<400> SEQUENCE: 3
tcttcctggg cacttacacc                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic Reverse Primer for Slc4a4 (mouse)

<400> SEQUENCE: 4
aggagcatac caccatgagg                                          20
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic Forward Primer for Car2 (mouse)

<400> SEQUENCE: 5
gatccttgct cccttcttcc                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Reverse Primer for Car2 (mouse)

<400> SEQUENCE: 6
atcacccagc ctaactgtgc                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Forward Primer for Col4a2 (mouse)

<400> SEQUENCE: 7
tggagttcct ggtttgaagg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Reverse Primer for Col4a2 (mouse)

<400> SEQUENCE: 8
tcaccaaagt ccccagtagg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Forward Primer for Col8a2 (mouse)

<400> SEQUENCE: 9
ggtccagtag gggctaaagg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Reverse Primer for Col8a2 (mouse)

<400> SEQUENCE: 10
cctgtaaaac ctggctcacc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Forward Primer for Cdh2 (mouse)
```

<400> SEQUENCE: 11
caggaaaagt ggcaggtagc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Reverse Primer for Cdh2 (mouse)

<400> SEQUENCE: 12
ataatgaaga tgcccgttgg                                               20

<210> SEQ ID NO 13
<211> LENGTH: 21
<212> TYPE: DNA
<213> ORGANISM: Artificial Sequence
<220> FEATURE:
<223> OTHER INFORMATION: Synthetic Forward Primer for Gapdh (mouse)

<400> SEQUENCE: 13
gaccacagtc catgccatca c                                             21

<210> SEQ ID NO 14
<211> LENGTH: 24
<212> TYPE: DNA
<213> ORGANISM: Artificial Sequence
<220> FEATURE:
<223> OTHER INFORMATION: Synthetic Reverse Primer for Gapdh (mouse)

<400> SEQUENCE: 14
agacaacctg gtcctcagtg tagc                                          24

<210> SEQ ID NO 15
<211> LENGTH: 20
<212> TYPE: DNA
<213> ORGANISM: Artificial Sequence
<220> FEATURE:
<223> OTHER INFORMATION: Synthetic Forward Primer for Atp1a1 (human)

<400> SEQUENCE: 15
ctacctggct tgctctgtcc                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Reverse Primer for Atp1a1 (human)

<400> SEQUENCE: 16
cgtctttcag ctcctcatcc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Forward Primer for Slc4a4 (human)

<400> SEQUENCE: 17
tgtgccaagt gagttcaagc                                               20

<210> SEQ ID NO 18

-continued

```
<211> LENGTH: 20
<212> TYPE: DNA
<213> ORGANISM: Artificial Sequence
<220> FEATURE:
<223> OTHER INFORMATION: Synthetic Reverse Primer for Slc4a4 (human)

<400> SEQUENCE: 18
actgtcgatg tgagcaatgg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Forward Primer for Car2 (human)

<400> SEQUENCE: 19
caatggtcat gctttcaacg                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Reverse Primer for Car2 (human)

<400> SEQUENCE: 20
caatccaggt cacacattcc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Forward Primer for Col4a2 (human)

<400> SEQUENCE: 21
tgcatgaaga acctgtgagc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Reverse Primer for Col4a2 (human)

<400> SEQUENCE: 22
tgctgttgtc tcgtctgtcc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Forward Primer for Col8a2 (human)

<400> SEQUENCE: 23
accctctggt tccaatttcc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Reverse Primer for Col8a2 (human)

<400> SEQUENCE: 24
```
tcagccagtc agaagtcagc                                                   20

<210> SEQ ID NO 25
<211> LENGTH: 20
<212> TYPE: DNA
<213> ORGANISM: Artificial Sequence
<220> FEATURE:
<223> OTHER INFORMATION: Synthetic Forward Primer for Cdh2 (human)

<400> SEQUENCE: 25
aggtttgcca gtgtgactcc                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic Reverse Primer for Cdh2 (human)

<400> SEQUENCE: 26
atgggtcttt catccattcg                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic Forward Primer for Atp1a1 (human)

<400> SEQUENCE: 27
gtcaaggctg agaacgggaa                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic Reverse Primer for Gapdh (human)

<400> SEQUENCE: 28
gcttcaccac cttcttgatg                                                   20

<210> SEQ ID NO 29
<211> LENGTH: 20
<212> TYPE: DNA
<213> ORGANISM: Artificial Sequence
<220> FEATURE:
<223> OTHER INFORMATION: Synthetic Forward Primer for Atp1a1 (human)

<400> SEQUENCE: 29
ccaaagacag ggtgctatcg                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic Reverse Primer for Atp1a1 (human)

<400> SEQUENCE: 30
ttgcttggac acatctgagc                                                   20

<210> SEQ ID NO 31
<211> LENGTH: 20
<212> TYPE: DNA

```
<213> ORGANISM: Artificial Sequence
<220> FEATURE:
<223> OTHER INFORMATION: Synthetic Forward Primer for Slc4a4 (human)

<400> SEQUENCE: 31
tgtgccaagt gagttcaagc                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic Reverse Primer for Slc4a4 (human)

<400> SEQUENCE: 32
actgtcgatg tgagcaatgg                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic Forward Primer for Car2 (human)

<400> SEQUENCE: 33
gatggaggat gaagctgtcc                                                    20

<210> SEQ ID NO 34
<211> LENGTH: 20
<212> TYPE: DNA
<213> ORGANISM: Artificial Sequence
<220> FEATURE:
<223> OTHER INFORMATION: Synthetic Reverse Primer for Car2 (human)

<400> SEQUENCE: 34
tgtaactctt cggcacatgg                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic Forward Primer for K8 (human)

<400> SEQUENCE: 35
ggaagctggt gtctgagtcc                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic Reverse Primer for K8 (human)

<400> SEQUENCE: 36
ctcctgttcc cagtgctacc                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic Forward Primer for K18 (human)

<400> SEQUENCE: 37
ggagcacttg gagaagaagg                                                    20
```

```
<210> SEQ ID NO 38
<211> LENGTH: 20
<212> TYPE: DNA
<213> ORGANISM: Artificial Sequence
<220> FEATURE:
<223> OTHER INFORMATION: Synthetic Reverse Primer for K18 (human)

<400> SEQUENCE: 38
aagtcatcag cagcaagacg                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic Forward Primer for Col4a2 (human)

<400> SEQUENCE: 39
acgagacaac agcacacagg                                            20

<210> SEQ ID NO 40
<211> LENGTH: 20
<212> TYPE: DNA
<213> ORGANISM: Artificial Sequence
<220> FEATURE:
<223> OTHER INFORMATION: Synthetic Reverse Primer for Col4a2 (human)

<400> SEQUENCE: 40
cggtatttgg gagaacatgg                                            20

<210> SEQ ID NO 41
<211> LENGTH: 20
<212> TYPE: DNA
<213> ORGANISM: Artificial Sequence
<220> FEATURE:
<223> OTHER INFORMATION: Synthetic Forward Primer for Col8a2 (human)

<400> SEQUENCE: 41
caagagkggt tcatctgtgg                                            20
```
(note: caagaggggt tcatctgtgg)
```
<210> SEQ ID NO 42
<211> LENGTH: 20
<212> TYPE: DNA
<213> ORGANISM: Artificial Sequence
<220> FEATURE:
<223> OTHER INFORMATION: Synthetic Reverse Primer for Col8a2 (human)

<400> SEQUENCE: 42
gtccagagcc aactcattcc                                            20

<210> SEQ ID NO 43
<211> LENGTH: 21
<212> TYPE: DNA
<213> ORGANISM: Artificial Sequence
<220> FEATURE:
<223> OTHER INFORMATION: Synthetic Forward Primer for Cdh2 (human)

<400> SEQUENCE: 43
tgacaacatt cactgctcag g                                          21

<210> SEQ ID NO 44
<211> LENGTH: 20
<212> TYPE: DNA
<213> ORGANISM: Artificial Sequence
<220> FEATURE:
```

<223> OTHER INFORMATION: Synthetic Reverse Primer for Cdh2 (human)

<400> SEQUENCE: 44
gattctcggt ccaaaacagc                                           20

<210> SEQ ID NO 45
<211> LENGTH: 20
<212> TYPE: DNA
<213> ORGANISM: Artificial Sequence
<220> FEATURE:
<223> OTHER INFORMATION: Synthetic Forward Primer for Cldn10b (human)

<400> SEQUENCE: 45
acggcacggt catcacaacc                                           20

<210> SEQ ID NO 46
<211> LENGTH: 21
<212> TYPE: DNA
<213> ORGANISM: Artificial Sequence
<220> FEATURE:
<223> OTHER INFORMATION: Synthetic Reverse Primer for Cldn10b (human)

<400> SEQUENCE: 46
gacagcagcg atcataagtc c                                         21

<210> SEQ ID NO 47
<211> LENGTH: 20
<212> TYPE: DNA
<213> ORGANISM: Artificial Sequence
<220> FEATURE:
<223> OTHER INFORMATION: Synthetic Forward Primer for Itga3 (human)

<400> SEQUENCE: 47
ggtgcctaca actggaaagg                                           20

<210> SEQ ID NO 48
<211> LENGTH: 20
<212> TYPE: DNA
<213> ORGANISM: Artificial Sequence
<220> FEATURE:
<223> OTHER INFORMATION: Synthetic Reverse Primer for Itga3 (human)

<400> SEQUENCE: 48
gcctacctgc atcgtgtacc                                           20

<210> SEQ ID NO 49
<211> LENGTH: 20
<212> TYPE: DNA
<213> ORGANISM: Artificial Sequence
<220> FEATURE:
<223> OTHER INFORMATION: Synthetic Forward Primer for Pitx2 (human)

<400> SEQUENCE: 49
gatgtgccaa aggtcagagg                                           20

<210> SEQ ID NO 50
<211> LENGTH: 20
<212> TYPE: DNA
<213> ORGANISM: Artificial Sequence
<220> FEATURE:
<223> OTHER INFORMATION: Synthetic Reverse Primer for Pitx2 (human)

<400> SEQUENCE: 50
attgcacggg atagaagtgg                                           20

```
<210> SEQ ID NO 51
<211> LENGTH: 20
<212> TYPE: DNA
<213> ORGANISM: Artificial Sequence
<220> FEATURE:
<223> OTHER INFORMATION: Synthetic Forward Primer for Gapdh (human)

<400> SEQUENCE: 51
aacggatttg gtcgtattgg                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic Reverse Primer for Gapdh (human)

<400> SEQUENCE: 52
catgggtgga atcatattgg                                               20
```